United States Patent [19]

Schödel

[11] 4,062,793
[45] Dec. 13, 1977

[54] CLEANING AGENTS FOR DENTURES

[75] Inventor: Christian Schödel, Mainz-Marienborn, Germany

[73] Assignee: Blendax-Werke R. Schneider GmbH & Co., Mainz, Germany

[21] Appl. No.: 723,891

[22] Filed: Sept. 16, 1976

Related U.S. Application Data

[63] Continuation of Ser. No. 541,012, Jan. 14, 1975, abandoned.

[51] Int. Cl.$^2$ .......................... C11D 7/56; C11D 7/38
[52] U.S. Cl. ............................................ 252/99; 252/95; 252/102; 252/106; 424/48; 424/54; 424/53; 424/78; 252/525; 252/541; 252/544

[58] Field of Search .................. 252/99, 95, 106, 102, 252/525, 541, 546; 424/78, 53, 48, 54

[56] References Cited

U.S. PATENT DOCUMENTS 3,957,967  5/1976  L'Orange ........................ 252/541 X

*Primary Examiner*—Mayer Weinblatt
*Attorney, Agent, or Firm*—Connolly and Hutz

[57] ABSTRACT

Disclosed is an improved denture cleaning agent containing a member selected from the group consisting of 1,6-di-(4-chlorophenyldiguanido)-hexane, 1,6-di-(2-ethylhexyldiguanido)-hexane, 1,6-di-(4-chlorobenzyldiguanido)-hexane, salts thereof or mixtures of two or more of such members.

4 Claims, No Drawings

CLEANING AGENTS FOR DENTURES

CROSS-REFERENCE TO RELATED APPLICATION

This application is a continuation application of Ser. No. 541,012, filed Jan. 14, 1975 now abandoned.

FIELD OF THE INVENTION

The object of cleaning agents for dentures is the complete and rapid cleaning of dentures, especially the removal of plaque built up on the denture surfaces between cleanings. The known preparations presently on the market do not completely fulfill this objective. The wearing of dentures not completely freed of plaque is not only unhygienic, it may also lead within a short time to a damage of the mucous membrane.

A need exists, therefore, for a cleaning agent for dentures which effects a fast and complete cleaning of the dentures of the food particles collected between cleanings and particularly of the plaque found thereon and, as much as possible, which also prevents at least for a limited time the recurrence of plaque on the dentures while they are worn.

BRIEF SUMMARY OF THE INVENTION

It has now been found in accord with the invention that the above objectives are achieved by a denture cleaning composition which contains about 10 to about 50 percent by weight (based on the total composition) of oxygen-releasing agents, about 5 to about 40 percent by weight complexing agents, optionally about 0.1 to about 10 percent by weight surface active agents and in addition thereto about 0.05 to about 25 percent by weight of at least one member selected from the group consisting of 1,6-di-(4-chlorophenyldiguanido)-hexane (known also under the common name "chlorohexidine"), 1,6-di-(2-ethylhexyldiguanido)hexane and/or 1,6-di-(4-chlorobenzyldiguanido)-hexane or the salts thereof (the amount used calculated in the case of salts on a free base). Depending upon the precise form of the cleaning agent, the remainder of the denture cleaning composition may comprise the usual fillers, alkaline-reacting substances, enzymes, preserving agents, thinning agents, binding agents, aromatics and flavoring agents and/or alcohols.

DETAILED DESCRIPTION OF THE INVENTION

The compositions according to the invention provide the required properties and consequently are clearly superior to the cleaning preparations previously known in this field. In addition, it has been shown that said denture cleaning agents prevent the so-called "bacterial corrosion" of synthetic materials used for dentures, as this is described, for example, by J. P. Engelhardt and L. Grun, Deutsche Zahnarztliche Zeitschrift (German Journal of Dentistry), Vol. 27 (1972), pp. 446-73. This "bacterial corrosion" is noticeable externally by a change in color of the dentures and by an unpleasant odor build-up, which in all probability is traced back to the effects of bacteria on the additives present in the denture material such as plasticizers or wetting agents.

The precise amount of diguanido-hexane used in accord with the present invention normally depends upon the form of application. When the denture cleaning agent is in the form of a solution, a paste or a gel, hence when it is intended for direct application to the denture, the concentration of chlorohexidine, 1,6-di-(2-ethylhexyldiguanido)-hexane and/or 1,6-di-(4-chlorobenzyldiguanido)-hexane or the salts thereof (calculated on a free base) usually ranges from about 0.05 to about 5 percent by weight of the total composition. If the novel cleaning agent for dentures is in the form of a powder or a tablet, the amount of diguanido-hexane or salt used then is about 0.05 to about 25 percent by weight.

Suitable oxidizing or oxygen-yielding compounds within the scope of the present invention are those agents which have already been suggested for this purpose in known denture cleaning compositions. Particularly preferred in this connection are the various alkali persulfates and alkali perborates such as potassium, ammonium, sodium, and lithium persulfates or perborates. However, other peroxides may also be used, e.g., alkali carbonate peroxide, alkali pyrophosphate peroxide, alkali peroxides, alkaline earth peroxides such as magnesium, calcium or even zinc peroxides as well as organic peroxides such as urea peroxide, benzoyl peroxide or lauroyl peroxide. Of course, it is also possible to use compositions of the known peroxides together or with other known peroxides.

Within the scope of the present invention, suitable complexing agents are preferably the water-soluble alkali polyphosphates, particularly sodium or potassium polyphosphates, alkali hexametaphosphate, tetrasodium pyrophosphate or organic complex constituents, e.g., nitrilotriacetic acid and the salts thereof, ethylene diaminotetra acetic acids, hydroxyethane diphosphonic acid and other polycarboxylic acid or the salts thereof which are well known and previously described for this purpose.

The novel cleaning agents for dentures furthermore may contain one or more surface-active substances. In theory, any of the well-known surface active agents may be used, but the use of anionic agents, because of their possible incompatibility with the biguanide derivatives, are less preferred. The proportion of surface active agent generally should not exceed about 2.5 percent by weight of the total composition.

Suitable anion-active tensides are, for example, higher alkylsulfates and the salts thereof, particularly sodium lauryl sulfate, salts of higher aliphatic acylamides of lower aliphatic amino acids, particularly N-lauroylsarcosinate or N-myristoyl sarcosinate, albuminous fatty acid condensates, alkylarylsulfonates, olefinsulfinates, long-chain alkylsulfoacetates, etc.

Suitable cation-active, non-ionic, and ampholytic tensides, which are completely compatible with chlorohexidine, are, for example, quaternary ammonium compounds such as cetyltrimethylammonium bromide, condensates of alkylene oxides such as ethylene or propylene oxide with fatty alcohols, phenols, fatty amines or fatty acid alkanolamides, fatty acid alkanolamides per se, esters of long-chain fatty acids and polyalcohols or sugars, e.g., glycerin monostearate or saccharose monolaurate or sorbitol polyoxyethylene mono or di-stearate, betains, sulfobetaines or long-chain alkylamino carboxylic acids.

In addition to the above constituents, the denture cleaning compositions of the present invention may also include alkaline substances such as trisodium phosphate, sodium, ammonium or potassium carbonates, alkali hydrogen carbonates, etc.

The novel cleaning agents for dentures may be colored and contain, in such instance, water-soluble coloring agents, which may also serve as time indicators, becoming colorless upon a completed cleaning.

Such coloring agents are, for example, FDC Blue 02, DC Red 010, FDC Green 01 and 02 or FDC Violet 01, all of which are introduced in an extremely small concentration.

When the novel agent is used in the form of a tablet, it will normally contain the usual binding agents, e.e., polyvinyl pyrrolidone.

If the novel agent is present in the form of a paste or a gel, it normally will contain thickening and gel-forming agents, e.g., various cellulose derivates such as carboxy, hydroxyethyl, methyl or ethyl cellulose.

The optional addition of flavoring and aromatic substances is well known and needs no further explanation as is the possible use of preserving agents, buffering substances, filling agents, thinning agents, or alcohols, e.g., dioles or glycerin.

For the disintegration of food residue and plaque, enzymes may be added to the novel agent, e.g., proteases, carbohydrases, particularly such which separate polysaccharides present in the plaque such as dextranase, "mutanase" and other α-glucaneglucanohydrolases.

In short, in addition to the diguanido-hexane derivatives of the present invention, the denture cleaning agent may contain the other ingredients commonly found in such compositions--see U.S. Pat. Nos. 2,498,344, 3,114,111, 3,337,466, 3,372,125 and 3,640,879.

In addition to chlorohexidine, 1,6-di-(2-ethylhexyl-diguanido)-hexane and/or 1,6-di-(4-chlorobenzyl-diguanido)-hexane per se, there may also be used one or more of the water-soluble salts thereof, as previously mentioned. Such salts in particular include the diacetate, the digluconate, the diformiate, the dilactate and the dipropionate salts, and, in addition, the dihydrochloride, the dihydrofluoride, the dibromide, the sulfate, the phosphate, the nitrate, the succinate, the pivalate, the citrate, the tartrate, the maleate, the malate, the disarcosinate, the monofluorophosphate or the hexafluorophosphate may be used.

Following are several examples describing the cleaning agents for dentures falling into the scope of the invention. The percent figures given relate entirely to percentages by weight of the total composition.

Example I
Cleaning Tablet

| Ingredients | Percent by Weight |
| --- | --- |
| potassium monopersulfate | 25.0 |
| sodiumperborate monohydrate | 43.0 |
| sodium tripolyphosphate | 20.4 |
| tetrasodium pyrophosphate | 5.0 |
| silicon dioxide, pyrogenic | 1.5 |
| aroma | 0.3 |
| polyethylene glycol 6000 | 1.8 |
| polyvinyl pyrrolidone | 2.5 |
| chlorohexidine hydrochloride (B.P.) | 0.5 |

Example II
Cleaning Tablet

| Ingredients | Percent by Weight |
| --- | --- |
| potassium monopersulfate | 12.5 |
| sodiumperborate monohydrate | 24.0 |
| potassium sodium tripolyphosphate | 16.0 |
| trisodium phosphate | 8.0 |
| polyethylene glycol 4000 | 5.0 |
| silicon dioxide, pyrogenic | 1.6 |
| peppermint oil | 0.3 |
| sodium hydrogen carbonate | 22.0 |
| tartaric acid | 9.6 |
| chlorohexidine diacetate (B.P.C.) | 1.0 |

Example III
Cleaning Tablet

| Ingredients | Percent by Weight |
| --- | --- |
| sodiumperborate monohydrate | 28.00 |
| sodium tripolyphosphate | 20.00 |
| trisodium phosphate | 12.00 |
| sodium carbonate | 17.50 |
| sodium hexametaphosphate | 5.00 |
| potassium monopersulfate | 7.00 |
| phenolphthalein | 0.02 |
| polyvinyl pyrrolidone | 6.50 |
| silicon dioxide, pyrogenic | 2.00 |
| aroma | 0.38 |
| 1,6-di(2-ethylhexyldiguanido)-hexane dihydrochloride | 1.10 |
| sodium benzoate | 0.50 |

Example IV
Cleaning Tablet

| Ingredients | Percent by Weight |
| --- | --- |
| sodium perborate monohydrate | 40.0 |
| potassium monopersulfate | 8.0 |
| sodium carbonate | 15.0 |
| sodium tripolyphosphate | 24.9 |
| chlorohexidine diacetate (B.P.C) | 1.8 |
| silicon dioxide, pyrogenic | 3.5 |
| peppermint oil | 0.5 |
| trisodium phosphate | 5.7 |
| proteases of *B. subtilis* | 0.6 |

Example V
Cleaning Powder

| Ingredients | Percent by Weight |
| --- | --- |
| potassium persulfate | 22.0 |
| urea peroxide | 15.0 |
| sodium bicarbonate | 15.0 |
| potassium tripolyphosphate | 22.5 |
| 1,6-di-(4-chlorobenzyldiguanido)-hexane dihydrochloride | 2.5 |
| sodium pyrophosphate | 3.1 |
| aromatic substances | 0.9 |
| sodium lauryl sulfate | 2.0 |
| dextranase of *P. funiculosum* | 2.5 |
| sodium sulfate | 14.5 |
| sodium carbonate | 10.0 |

Throughout the specification and claims, the term "denture" means a dental prosthetic device including artificial teeth, removable orthodontic bridges and denture plates of both upper and lower types, full or partial.

What is claimed is:

1. A cleaning composition for dentures consisting essentially of from about 10 to about 50 percent by weight of an oxygen-releasing agent, about 5 to about 40 percent by weight of a complexing agent and from about 0.05 to about 25 percent by weight of at least one member selected from the group consisting of 1,6-di-(4-chlorophenyldiguanido)-hexane, 1,6-di-(2-ethylhexyl-diguanido)-hexane, 1,6-di-(4-chlorobenzyldiguanido)-hexane and the water soluble salts thereof.

2. The cleaning agent according to claim 1 containing from about 0.5 to about 10 percent by weight of a surface active agent.

3. The cleaning composition according to claim 1 in the form of a tablet or a powder containing from about 0.5 to about 25 percent by weight of at least one member selected from the group consisting of 1,6-di-(4-chlorophenyldiguanido)-hexane, 1,6-di-(2-ethylhexyl-diguanido)-hexane, 1,6-di-(4-chlorobenzyldiguanido)-hexane and the water soluble salts thereof.

4. The cleaning composition according to claim 1 in the form of a solution, a paste or a gel containing from about 0.05 to about 5 percent by weight of at least one member selected from the group consisting of 1,6-di-(4-chlorophenyldiguanido)-hexane, 1,6-di-(2-ethylhexyl-diguanido)-hexane, 1,6-di-(4-chlorobenzyldiguanido)-hexane and the water soluble salts thereof.

* * * * *